(12) United States Patent
Nick et al.

(10) Patent No.: US 10,689,703 B2
(45) Date of Patent: Jun. 23, 2020

(54) METHODS OF IDENTIFYING AND TREATING SUBJECTS HAVING ACUTE RESPIRATORY DISTRESS SYNDROME

(71) Applicant: National Jewish Health, Denver, CO (US)

(72) Inventors: Jerry A. Nick, Denver, CO (US); Kenneth C. Malcolm, Denver, CO (US)

(73) Assignee: National Jewish Health, Denver, CO (US)

( * ) Notice: Subject to any disclaimer, the term of this patent is extended or adjusted under 35 U.S.C. 154(b) by 127 days.

(21) Appl. No.: 15/139,119

(22) Filed: Apr. 26, 2016

(65) Prior Publication Data

US 2016/0312285 A1    Oct. 27, 2016

Related U.S. Application Data

(60) Provisional application No. 62/153,059, filed on Apr. 27, 2015.

(51) Int. Cl.
| | |
|---|---|
| *C12Q 1/68* | (2018.01) |
| *A61K 38/00* | (2006.01) |
| *A61K 38/21* | (2006.01) |
| *A61K 39/395* | (2006.01) |
| *C12Q 1/6883* | (2018.01) |
| *G16B 25/00* | (2019.01) |

(52) U.S. Cl.
CPC .......... *C12Q 1/6883* (2013.01); *G16B 25/00* (2019.02); *C12Q 2600/106* (2013.01); *C12Q 2600/112* (2013.01); *C12Q 2600/158* (2013.01)

(58) Field of Classification Search
None
See application file for complete search history.

(56) References Cited

U.S. PATENT DOCUMENTS 8,163,885 B2 *   4/2012   Svensson ............. C07K 16/249
530/388.2

OTHER PUBLICATIONS

Dejager et al., The Journal of Infectious Diseases 209(6): 960-970 (Year: 2014).*
NCT00548795, (2007), pp. 1-6 (Year: 2007).*
Calfee et al. "Active and Passive Cigarette Smoking and Acute Lung Injury after Severe Blunt Trauma," American Journal of Respiratory and Critical Care Medicine, Jun. 2011, vol. 183, No. 12, pp. 1660-1665.
Fialkow et al. "Neutrophil apoptosis: a marker of disease severity in sepsis and sepsis-induced acute respiratory distress syndrome," Critical Care, Nov. 2006, vol. 10, No. 6, R155, 14pages.
Gao et al. "Recent advances in genetic predisposition to clinical acute lung injury," American Journal of Physiology Lung Cellular and Molecular Physiology, May 2009, vol. 296, No. 5, pp. L713-L725.
Hudson et al. "Clinical Risks for Development of the Acute Respiratory Distress Syndrome," American Journal of Respiratory and Critical Care Medicine, Feb. 1995, vol. 151, No. 2, pp. 293-301.
Irabarren et al. "Cigarette Smoking, Alcohol Consumption, and Risk of ARDS," CHEST, Jan. 2000, vol. 117, No. 1, pp. 163-168.
Kangelaris et al. "The Association Between a Darc Gene Polymorphism and Clinical Outcomes in African American Patients With Acute Lung Injury," CHEST, May 2012, vol. 141, No. 5, pp. 1160-1169.
Lee et al. "Evaluation of broncoalveolar lavage fluid from ARDS patients with regard to apoptosis," Respiratory Medicine, Mar. 2008, vol. 102, No. 3, pp. 464-469.
Malcolm et al. "Bacteria-Specific Neutrophil Dysfunction Associated with Interferon-Stimulated Gene Expression in the Acute Respiratory Distress Syndrome," PLoS ONE, Jul. 2011, vol. 6, No. 7, e 21958, 12 pages.
Matthay "The acute respiratory distress syndrome," The Journal of Clinical Investigation, Aug. 2012, vol. 122, No. 8, pp. 2731-2740.
Metz et al. "Interferon-stimulated genes and their role in controlling hepatitis C virus," Journal of Hepatology, Dec. 2013, vol. 59, No. 6, pp. 1331-1341.
Ramilo et al. "Gene expression patterns in blood leukocytes discriminate patients with acute infections," Blood, Mar. 2007, vol. 109, No. 5, pp. 2066-2077.
Roers et al. "MxA Gene Expression after Live Virus Vaccination: A Sensitive Marker for Endogenous Type I Interferon," The Journal of Infectious Diseases, Apr. 1994, vol. 169, No. 4, pp. 807-813.
Zaas et al. "Gene Expression Signatures Diagnose Influenza and Other Symptomatic Respiratory Viral Infection in Humans," Cell Host Microbe, Sep. 2009, vol. 6, No. 3, pp. 207-217.

* cited by examiner

*Primary Examiner* — Daniel E Kolker
*Assistant Examiner* — Jegatheesan Seharaseyon
(74) *Attorney, Agent, or Firm* — Sheridan Ross P.C.

(57) ABSTRACT

The present invention is related to novel methods for categorizing and treating subjects having Acute Respiratory Distress Syndrome (ARDS).

3 Claims, 4 Drawing Sheets

Specification includes a Sequence Listing.

SEQUENCE LISTING

<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: IFIT1 forward primer

<400> SEQUENCE: 1
agaacggctg cctaatttac a                                        21

<210> SEQ ID NO 2
<211> LENGTH: 21
<212> TYPE: DNA
<213> ORGANISM: Artificial Sequence
<220> FEATURE:
<223> OTHER INFORMATION: IFITI reverse primer

<400> SEQUENCE: 2
gctccagact atccttgacc t                                        21

METHODS OF IDENTIFYING AND TREATING SUBJECTS HAVING ACUTE RESPIRATORY DISTRESS SYNDROME

CROSS-REFERENCE TO RELATED APPLICATIONS

This application claims the benefit of priority under 35 U.S.C. § 119(e) to U.S. Provisional Patent Application No. 62/153,059, filed Apr. 27, 2015. The entire disclosure of U.S. Provisional Patent Application No. 62/153,059 is incorporated herein by reference.

GOVERNMENT SUPPORT

This invention was made with government support under grant number R01HL090991 awarded by the National Institutes of Health. The government has certain rights in the invention.

REFERENCE TO A SEQUENCE LISTING

This application contains a Sequence Listing submitted electronically as a text file by EFS-Web. The text file, named "2879-189_ST25", has a size in bytes of 1 KB, and was recorded on Apr. 26, 2016. The information contained in the text file is incorporated herein by reference in its entirety pursuant to 37 CFR § 1.52(e)(5).

FIELD OF THE INVENTION

The present invention is directed toward the categorization or identification and treatment of subjects that have Acute Respiratory Distress Syndrome (ARDS) and/or are at risk for a severe form of Acute Respiratory Distress Syndrome (ARDS).

BACKGROUND OF THE INVENTION

Extensive variability in severity and survival is a common feature of acute respiratory distress syndrome (ARDS), and identification of mechanisms that regulate this variability may lead to more personalized treatment. Age, race, cigarette smoking, and alcoholism impair the immune system, and are linked to increased prevalence or worse ARDS outcomes (Iribarren C, et al. (2000) Cigarette smoking, alcohol consumption, and risk of ARDS: a 15-year cohort study in a managed care setting. Chest 117: 163-168.; Calfee C S, et al. (2011) Active and passive cigarette smoking and acute lung injury after severe blunt trauma. Am J Respir Crit Care Med 183: 1660-1665.; Hudson L, et al. (1995) Clinical risk for development of the acute respiratory distress syndrome. Am J Respir Crit Care Med 151: 293-301.; Moss M, et al. (1996) The role of chronic alcohol abuse in the development of acute respiratory distress syndrome in adults. Jama 275: 50-54.; Milberg J A, et al. (1995) Improved survival of patients with acute respiratory distress syndrome (ARDS): 1983-1993. Jama 273: 306-309.; Ely E W, et al. (2002) Recovery rate and prognosis in older persons who develop acute lung injury and the acute respiratory distress syndrome. Ann Intern Med 136: 25-36.; Kangelaris K N, et al. (2012) The association between a Darc gene polymorphism and clinical outcomes in African American patients with acute lung injury. Chest 141: 1160-1169.; Moss M, Mannino D M (2002) Race and gender differences in acute respiratory distress syndrome deaths in the United States: an analysis of multiple-cause mortality data (1979-1996). Crit Care Med 30: 1679-1685.; Rubenfeld G D, et al. (2005) Incidence and outcomes of acute lung injury. N Engl J Med 353: 1685-1693.). Specific forms of inflammatory dysregulation are also linked to worse outcomes from sepsis or ARDS, including coding variations in over 25 genes (Matthay M A, Ware L B, Zimmerman G A (2012) The acute respiratory distress syndrome. J Clin Invest 122: 2731-2740.; Gao L, Barnes K C (2009) Recent advances in genetic predisposition to clinical acute lung injury. Am J Physiol Lung Cell Mol Physiol 296: L713-725.; Arcaroli J, et al. (2005) Genetic Polymorphisms And Sepsis. Shock 24: 300-312.). ARDS is most commonly precipitated by pneumonia or sepsis (Rubenfeld G D, et al. (2005) Incidence and outcomes of acute lung injury. N Engl J Med 353: 1685-1693.; Ware L B, Matthay M A (2000) The acute respiratory distress syndrome. N Engl J Med 342: 1334-1349.), resulting in massive neutrophil accumulation within the pulmonary vasculature (Abraham E (2003) Neutrophils and acute lung injury. Crit Care Med 31: S195-199.). Both over-exuberant or diminished innate immune response to bacterial products can worsen clinical outcomes, as the protective benefit of pathogen killing is balanced against the considerable injurious capacity of neutrophils (Lamb N J, et al. (1999) Oxidative damage to proteins of BAL fluid in patients with ARDS: Evidence for neutrophil-mediated hydroxylation, nitration, and chlorination. Critical Care Medicine 27: 1738-1744.; Borregaard N, Cowland J B (1997) Granules of the Human Neutrophilic Polymorphonuclear Leukocyte. Blood 89: 3503-3521.). Various stimuli may evoke complex "adaptive" responses to pathogens by neutrophils, by either decreasing (tolerance) or increasing (priming) activation (Buckley J M, Wang J H, Redmond H P (2006) Cellular reprogramming by gram-positive bacterial components: a review. J Leukoc Biol 80: 731-741.; Fan H, Cook J A (2004) Molecular mechanisms of endotoxin tolerance. J Endotoxin Res 10: 71-84.). Neutrophil function appears dysregulated in ARDS (Lee K S, et al. (2008) Evaluation of bronchoalveolar lavage fluid from ARDS patients with regard to apoptosis. Respir Med 102: 464-469.; Aggarwal A, (2000) G-CSF and IL-8 but not GM-CSF correlate with severity of pulmonary neutrophilia in acute respiratory distress syndrome. Eur Respir J 15: 895-901.; Goodman R B, et al. (1996) Inflammatory cytokines in patients with persistence of the acute respiratory distress syndrome. Am J Respir Crit Care Med 154: 602-611.; Lesur O, et al. (2000) Interleukin-2 involvement in early acute respiratory distress syndrome: relationship with polymorphonuclear neutrophil apoptosis and patient survival. Crit Care Med 28: 3814-3822.; Mascellino M T, et al. (2001) Reduced bactericidal activity against *Staphylococcus aureus* and *Pseudomonas aeruginosa* of blood neutrophils from patients with early adult respiratory distress syndrome. J Med Microbiol 50: 49-54.; Martin T R, et al. (1991) The function of lung and blood neutrophils in patients with the adult respiratory distress syndrome. Implications for the pathogenesis of lung infections. Am Rev Respir Dis 144: 254-262.; Rivkind A I S J, et al. (1991) Neutrophil oxidative burst activation and the pattern of respiratory physiologic abnormalities in the fulminant post-traumatic adult respiratory distress syndrome. Circ Shock 33: 48-62.; Fialkow L, et al. (2006) Neutrophil apoptosis: a marker of disease severity in sepsis and sepsis-induced acute respiratory distress syndrome. Crit Care 10: R155.), and the potential exists that a beneficial adaptation to one microbe may place the host at a disadvantage against other infectious agents or inflammatory insults.

Viral infections can modify the immune response to subsequent bacterial infections (McNamee L A, Harmsen A G (2006) Both influenza-induced neutrophil dysfunction and neutrophil-independent mechanisms contribute to increased susceptibility to a secondary *Streptococcus pneumoniae* infection. Infect Immun 74: 6707-6721.; Brundage J F (2006) Interactions between influenza and bacterial respiratory pathogens: implications for pandemic preparedness. Lancet Infect Dis 6: 303-312.; Brundage J F, Shanks G D (2008) Deaths from bacterial pneumonia during 1918-19 influenza pandemic. Emerg Infect Dis 14: 1193-1199.; Metzger D W, Sun K (2013) Immune dysfunction and bacterial coinfections following influenza. J Immunol 191: 2047-2052.; Sun K, Metzger D W (2008) Inhibition of pulmonary antibacterial defense by interferon-gamma during recovery from influenza infection. Nat Med 14: 558-564.; Rothberg M B, et al. (2008) Complications of viral influenza. Am J Med 121: 258-264.; Sellers T F, et al. (1961) The influence of influenza virus infection on exogenous staphylococcal and endogenous murine bacterial infection of the bronchopulmonary tissues of mice. J Exp Med 114: 237-256.; McCullers J A (2006) Insights into the interaction between influenza virus and pneumococcus. Clin Microbiol Rev 19: 571-582.), and thus could predispose to ARDS. A principal immune response to viral infections is production of the Type I interferons (IFNα and IFNβ), which are evoked by a broad range of viral factors, and in turn upregulate expression of interferon-stimulated genes (ISG) (Stetson D B, Medzhitov R (2006) Type 1 interferons in host defense. Immunity 25: 373-381.; Roers A, et al. (1994) MxA gene expression after live virus vaccination: a sensitive marker for endogenous type I interferon. J Infect Dis 169: 807-813.; Halminen M, et al. (1997) Expression of MxA protein in blood lymphocytes discriminates between viral and bacterial infections in febrile children. Pediatr Res 41: 647-650.; Ramilo O, et al. (2007) Gene expression patterns in blood leukocytes discriminate patients with acute infections. Blood 109: 2066-2077.; Zaas A K, et al. (2009) Gene expression signatures diagnose influenza and other symptomatic respiratory viral infections in humans. Cell Host Microbe 6: 207-217.). Hundreds of diverse ISG have been identified, with gene products which may act to reduce viral replication and release (Metz P, Reuter A, Bender S, Bartenschlager R (2013) Interferon-stimulated genes and their role in controlling hepatitis C virus. J Hepatol 59: 1331-1341.), or alternatively function as inflammatory cytokine (Stetson D B, Medzhitov R (2006) Type 1 interferons in host defense. Immunity 25: 373-381.; Schoggins J W, et al. (2011) A diverse range of gene products are effectors of the type I interferon antiviral response. Nature 472: 481-485.; Pichlmair A, Reis e Sousa C (2007) Innate recognition of viruses. Immunity 27: 370-383.). However, ISG upregulation is neither sensitive nor specific for viral infection. Not all viral infections trigger the response, and certain intracellular bacteria or systemic autoimmune disorders have also been associated with IFNα/β release and ISG upregulation (Stetson D B, Medzhitov R (2006) Type 1 interferons in host defense. Immunity 25: 373-381.; Parker D, et al. (2014) Induction of type I interferon signaling determines the relative pathogenicity of *Staphylococcus aureus* strains. PLoS Pathog 10: e1003951.). In animal models and human neutrophils, elevated IFNα/β release and/or ISG expression has been reported to be associated with impaired response to specific bacteria (Parker D, et al. (2014) Induction of type I interferon signaling determines the relative pathogenicity of *Staphylococcus aureus* strains. PLoS Pathog 10: e1003951.; Mancuso G, et al. (2007) Type I IFN signaling is crucial for host resistance against different species of pathogenic bacteria. J Immunol 178: 3126-3133.; Carrero J A, Calderon B, Unanue E R (2004) Type I interferon sensitizes lymphocytes to apoptosis and reduces resistance to *Listeria* infection. J Exp Med 200: 535-540.; O'Connell R M, et al. (2004) Type I interferon production enhances susceptibility to *Listeria monocytogenes* infection. J Exp Med 200: 437-445.; Kelly-Scumpia K M, et al. (2010) Type I interferon signaling in hematopoietic cells is required for survival in mouse polymicrobial sepsis by regulating CXCL10. J Exp Med 207: 319-326.; Malcolm K C, et al. (2011) Bacteria-Specific Neutrophil Dysfunction Associated with Interferon-Stimulated Gene Expression in the Acute Respiratory Distress Syndrome. PLoS 6: e21958.). Conversely, severe bacterial-induced inflammation can suppress Type I IFN-regulated pathways, and certain viruses have acquired virulence factors which inhibit ISG (Brukman A, Enquist L W (2006) Suppression of the interferon-mediated innate immune response by pseudorabies virus. J Virol 80: 6345-6356.; Eidson K M, et al. (2002) Expression of herpes simplex virus ICP0 inhibits the induction of interferon-stimulated genes by viral infection. J Virol 76: 2180-2191.; Kotla S, et al. (2008) Attenuation of the type I interferon response in cells infected with human rhinovirus. Virology 374: 399-410.; Kumthip K, et al. (2012) Hepatitis C virus NS5A disrupts STAT1 phosphorylation and suppresses type I interferon signaling. J Virol 86: 8581-8591.; Ivashkiv L B, Donlin L T (2014) Regulation of type I interferon responses. Nat Rev Immunol 14: 36-49.; Bode J G, Brenndorfer E D, Haussinger D (2007) Subversion of innate host antiviral strategies by the hepatitis C virus. Arch Biochem Biophys 462: 254-265.). Together, these findings suggest that both elevated and suppressed ISG expression is associated with more severe outcomes in ARDS. However, it is noted that variability in the severity and duration of Acute Respiratory Distress Syndrome (ARDS) is incompletely understood, and has not been associated with Interferon-stimulated genes (ISG) expression.

SUMMARY OF THE INVENTION

One embodiment of the invention relates to a method of treating Acute Respiratory Distress Syndrome (ARDS) in a subject having been diagnosed as having ARDS comprising determining the expression level of one or more interferon-stimulated genes (ISGs) in a sample from the subject; comparing the expression level of the one or more ISGs of the subject with a control expression level, wherein an increase or decrease in the expression level of the ISGs from the subject as compared to the control expression levels identifies the subject as having s severe form ARDS; and treating the subject.

In one aspect, the subject having an increased ISG expression level is treated by administering to the subject a therapeutic effective amount of a pharmaceutical composition comprising an ISG suppressing agent.

In yet another aspect, the subject having a decreased ISG expression level is treated by administering to the subject a therapeutic effective amount of a pharmaceutical composition comprising an ISG enhancing agent.

In another aspect, the subject has been diagnosed or deemed to be at risk for a condition selected from the group consisting of sepsis and bacterial pneumonia.

Another embodiment of the present invention relates to a method of determining a treatment strategy for treating a subject having been diagnosed as having ARDS comprising determining the determining the expression level of one or more interferon-stimulated genes (ISGs) in a sample from the subject; comparing the expression level of the one or more ISGs of the subject with a control expression level, wherein an increase or decrease in the expression level of the ISGs from the subject as compared to the control expression level identifies the subject has having a severe form of ARDS; and treating the subject with a treatment strategy for severe ARDS comprising administering to the subject a therapeutic effective amount of an ISG suppressing agent if the subject's ISG expression level is greater than one standard deviation from the mean as compared to the control, or administering to the subject a therapeutic effective amount of an ISG enhancing agent if the subject's ISG expression level is less than one standard deviation from the mean as compared to the control.

Another embodiment of the present invention relates to a method of quantifying the overall gene expression level of the combination of MX1, IFIT1, and ISG15 in a sample from a subject having ARDS comprising extracting RNA from a sample obtained from the patient; quantifying the relative gene expression level of each of MX1, IFIT1, and ISG15 in the extracted RNA by quantitative PCR using primer pairs consisting of a first primer pair having ID No. Hs00182073_m1 (Applied BioSystems) for MX1; a second primer pair having ID No. Hs00192713_m1 (Applied BioSystems) for ISG15; and a third primer pair consisting of a forward primer consisting of SEQ ID NO:1 and a first reverse primer consisting of SEQ ID NO:2; log transform each relative gene expression level by multiplying each relative gene expression level by $10^5$; and averaging the log transformed expression values to quantify the overall gene expression level.

In one aspect, the method further comprises comparing the overall gene expression level against a control expression level, wherein an altered overall gene expression level as compared to the control indicates the subject has a severe form of ARDS; wherein the overall gene expression level is altered if the level is greater than or less than one standard deviation from the mean as compared to the control expression level.

Another embodiment of the present invention relates to a method to diagnose severe ARDS in a subject in need thereof comprising extracting RNA from a sample obtained from the subject; determining the relative expression level of one or more interferon-stimulated genes (ISGs) in the RNA, wherein the ISGs are selected from the group consisting of MX1, IFIT1, ISG15 and combinations thereof, using at least one primer pair having ID No. Hs00182073_m1 for MX1; a second primer pair having ID No. Hs00192713_m1 for ISG15; and a third primer pair consisting of a forward primer consisting of SEQ ID NO:1 and a first reverse primer consisting of SEQ ID NO:2; log transform each relative gene expression level from step b by multiplying each relative gene expression level by $10^5$; averaging the log transformed expression values to quantify the overall gene expression level; comparing the overall gene expression level against a control expression level to determine whether the expression levels of MX1, IFIT1, ISG16 and combinations thereof are altered as compared to control expression level; wherein an altered expression level indicates the subject has severe ARDS. In one aspect, the overall expression level is altered when the overall expression level is increased or decreased by greater than or less than one standard deviation from the mean as compared to the control expression level.

In any of the above embodiments, determining the expression level of the one or more ISGs comprises extracting RNA from the sample and determining the expression level of the one or more ISGs in the extracted RNA by quantitative PCR. The control expression level is the mean expression level of the same ISGs predetermined from a reference level known to correlate with severe ARDS. An increase expression level occurs when the subject's ISG expression level is greater than one standard deviation from the mean as compared to the control. A decrease expression level occurs when the subject's ISG expression level is less than one standard deviation from the mean as compared to the control.

In any of the above embodiments, the ISGs are selected from the group consisting of MX1, IFIT1, ISG15 and combinations thereof.

In any of the above embodiments, the sample is selected from the group consisting of peripheral blood mononuclear cells (PBMCs), whole blood, leuokocytes, neutrophils, monocytes, lymphocytes, basophils, and eosinphils.

In any of the above embodiments, the control expression level is the mean expression level of the same ISGs predetermined from a reference level known to correlate with severe ARDS.

BRIEF DESCRIPTION OF THE DRAWINGS

FIG. 3A and FIG. 3B show the Kaplan-Meier Analysis of 90-Day Survival and Discharge to Home with Unassisted Breathing.

FIG. 4A, FIG. 4B and FIG. 4C show the association of ISG expression with confirmed viral infections and circulating IFNα.

DETAILED DESCRIPTION OF THE INVENTION

The present invention generally relates to novel methods for predicting, categorizing and/or treating subjects having ARDS as well as those with severe ARDS. The invention includes the use of ISG gene biomarkers whose expression patterns have been found to correlate with ARDS severity including worse clinical outcomes and an increase in mortality. As disclosed in the examples below, in a training set of ARDS patients and healthy volunteers, hierarchical clustering of neutrophil interferon-stimulated genes (ISGs) demonstrated the presence of 3 distinct cohorts with high, mid-range, or low ISG expression. The three ISGs with greatest variability in expression were selected for a 3-gene panel (myxovirus resistance 1 (MX1), interferon-stimulated 15 kDa protein (ISG15), and interferon-induced protein with tetratricopeptide repeats 1 (IFIT1)), and the capacity of these genes to predict clinical outcomes was tested at the onset of ARDS. As seen in the training set, a subgroup of patients with ARDS in the test set demonstrated relatively high ISG expression that was also seen in several healthy volunteers. A subgroup of ARDS patients also demonstrated relatively depressed ISG expression, not seen in healthy volunteers. ARDS patients with either high or low ISG expression demonstrated worse clinical outcomes and greater mortality (i.e. more severe or a more severe form of ARDS) than patients in the mid-range, after accounting for age, race, gender or body mass index (BMI). These findings identify ISG expression as a contributor to variability in ARDS disease severity and a marker of prognosis at time of presentation of ARDS. In addition, these findings provide different treatment options or strategies for patients based on the ISG expression group they belong to.

The present invention provides for a method of treating Acute Respiratory Distress Syndrome (ARDS) in a subject having been diagnosed as having ARDS. The method comprises detecting the expression level one or more Interferon-stimulated genes (ISG) in a sample from the subject, wherein an increased or decreased expression level of the ISGs as compared to a control level, identifies the subject as having a severe form of ARDS. The method further comprises treating the subject identified as having a severe form of ARDS.

The present invention also provides for a method of determining a treatment strategy for treating a subject having been diagnosed as having Acute Respiratory Distress Syndrome (ARDS). The method comprises determining the expression level of one or more interferon-stimulated genes (ISGs) in a sample from the subject; comparing the expression level of the one or more ISGs of the subject with a control expression level, wherein an increase or decrease in the expression level of the ISGs from the subject as compared to the control expression level identifies the subject has having a severe form of ARDS; and treating the subject with a treatment strategy for severe ARDS comprising administering to the subject a therapeutic effective amount of an ISG suppressing agent if the subject's ISG expression level is greater than one standard deviation from the mean as compared to the control, or administering to the subject a therapeutic effective amount of an ISG enhancing agent if the subject's ISG expression level is less than one standard deviation from the mean as compared to the control.

The present invention also provides for a method of quantifying the overall gene expression level of the combination of MX1, IFIT1, and ISG15 in a sample from a subject having ARDS. The method comprises extracting RNA from a sample obtained from the patient; quantifying the relative gene expression level of each of MX1, IFIT1, and ISG15 in the extracted RNA by quantitative PCR using primer pairs consisting of: a first primer pair having ID No. Hs00182073_m1 for MX1; a second primer pair having ID No. Hs00192713_m1 for ISG15; and a third primer pair consisting of a forward primer consisting of SEQ ID NO:1 and a first reverse primer consisting of SEQ ID NO:2; log transform each relative gene expression level by multiplying each relative gene expression level by $10^5$; and averaging the log transformed expression values to quantify the overall gene expression level.

The present invention also provides for a method to diagnose severe ARDS in a subject in need thereof. The method comprises extracting RNA from a sample obtained from the subject; determining the relative expression level of one or more interferon-stimulated genes (ISGs) in the RNA, wherein the ISGs are selected from the group consisting of MX1, IFIT1, ISG15 and combinations thereof, using at least one primer pair having ID No. Hs00182073_m1 for MX1; a second primer pair having ID No. Hs00192713_m1 for ISG15; and a third primer pair consisting of a forward primer consisting of SEQ ID NO:1 and a first reverse primer consisting of SEQ ID NO:2; log transform each relative gene expression level from by multiplying each relative gene expression level by $10^5$; averaging the log transformed expression values to quantify the overall gene expression level; comparing the overall gene expression level against a control expression level to determine whether the expression levels of MX1, IFIT1, ISG16 and combinations thereof are altered as compared to control expression level; wherein an altered expression level indicates the subject has severe ARDS.

The present invention also provides for a method for predicting the clinical outcome of a subject diagnosed with ARDS comprising detecting the expression level of one or more ISG in a sample from the subject, wherein an increased or decreased expression level as compared to a control level, predicts a poor prognosis and/or increased mortality of the subject.

The present invention further provides for a method for categorizing a subject at risk of severe ARDS comprising detecting the expression level of one or more ISG in a sample from the subject; comparing the expression of the one or more ISG genes from the subject with gene expression profiles of the same ISG genes known to correlate with severe ARDS, and categorizing the subject as at increased risk of severe ARDS when the subject's gene expression profile correlates to the gene expression profile for severe ARDS.

The present invention also provides for a method to treat a subject having severe ARDS comprising detecting the expression level one or more Interferon-stimulated genes (ISG), wherein an increased or decreased expression level as compared to a control level identifies the subject as having severe ARDS and treating the subject.

Methods of treating subjects having severe ARDS (or a severe form of ARDS) include but are not limited to increasing or decreasing ISG gene expression in the subject identified as having severe ARDS. For example, the subject who has a decreased ISG expression level may be administered an ISG enhancing agent, including but not limited to Type I interferons (IFN-alpha or IFN-beta), and Type III interferons. In another example, the subject who has an increased ISG expression level may be administered an ISG suppressing agent, including but not limited to an antibody that blocks interferon, inhibitors of viral recognition receptors (Toll-like receptors (TLR)-3, TLR-7, TLR-8, Retinoic Acid inducible gene-1 (RIG-1), melanomia differentiation-association protein 5 (MDA5), and DNA-Dependent activator of IFN-regulatory factors (DAI)), agents that neutralize circulating IFN-alpha or IFN-beta or their corresponding receptors (IFN-AR1 and IFN-AR2) and agents that suppress ISG expression through virus-stimulated pathways. If agents that suppress ISG expression through virus-stimulated pathways are used, treatment would be focused on the specific virus, including but not limited to anti-viral agents against influenza, HIV, hepatitis, varicella. Such anti-viral agents include but are not limited to amantidine and oseltamivir.

The ISG suppressing agents and ISG enhancing agents can be administered to the subject in a therapeutic effective amount such as in a pharmaceutical composition. The route of administration may be oral, intravenous, intranasal or inhaled.

In some cases patients with ARDS may recover quickly (within 48-72 hours), allowing them to breath without use of a ventilator (i.e. assisted breathing), be discharged from an intensive care unit (ICU) in a few days, then discharged from the hospital, and then ultimately to home. A subject with severe ARDS (or severe form of ARDS) may require prolonged dependence on mechanical ventilation, remain in the ICU for weeks, have a higher rate of mortality and a lower rate of discharge from a care center (such as a hospital and/or urgent care facility) to home, as compared to subjects that do not have severe ARDS.

A patient or subject sample includes any bodily fluid or tissue from a patient that may contain the RNA or protein encoded by the genes contemplated here. The term "sample" or "patient sample" or "subject sample" or "test sample" can be used generally to refer to a sample of any type which contains products that are to be evaluated by the present method, including but not limited to, a sample of isolated cells, a tissue sample and/or a bodily fluid sample. According to the present invention, a sample of isolated cells is a specimen of cells, typically in suspension or separated from connective tissue which may have connected the cells within a tissue in vivo, which have been collected from an organ, tissue or fluid by any suitable method which results in the collection of a suitable number of cells for evaluation by the method of the present invention. The cells in the cell sample are not necessarily of the same type, although purification methods can be used to enrich for the type of cells that are preferably evaluated. Cells can be obtained, for example, by scraping of a tissue, processing of a tissue sample to release individual cells, or isolation from a bodily fluid.

In some aspects, the sample may comprise blood, sputum, or bronchoalveolar lavage. In still some aspects the sample may comprise whole blood, Peripheral Blood Mononuclear Cells (PBMCs), neutrophils, leuokocytes, monocytes, lymphocytes, basophils, and/or eosinophils.

In some aspects, the subject has been diagnosed as having sepsis and/or bacterial pneumonia and/or has been deemed to be at risk for sepsis and/or bacterial pneumonia. In addition, it is contemplated herein that the methods presented herein could be used to determine if a subject has sepsis and/or bacterial pneumonia as well as to determine the severity of these conditions.

As used herein, the term "expression", when used in connection with detecting the expression of a gene, can refer to detecting transcription of the gene (i.e., detecting mRNA levels) and/or to detecting translation of the gene (detecting the protein produced). To detect expression of a gene refers to the act of actively determining whether a gene is expressed or not. This can include determining whether the gene expression is upregulated as compared to a control or reference, downregulated as compared to a control or reference, or unchanged as compared to a control or increased or decreased as compared to a reference level.

Expression of transcripts and/or proteins is measured by any of a variety of known methods in the art. For RNA expression, methods include but are not limited to: extraction of cellular mRNA and Northern blotting using labeled probes that hybridize to transcripts encoding all or part of the gene; amplification of mRNA using gene-specific primers, polymerase chain reaction (PCR), and reverse transcriptase-polymerase chain reaction (RT-PCR), quantitative PCR, and/or RNA Ampliseq, followed by quantitative detection of the product by any of a variety of means; multiplexed quantitative PCR enrichment of cDNA amplicons, followed by conversion of amplicons to sequence libraries and Next-generation based sequencing of libraries to generate digital count expression data; extraction of total RNA from the cells, which is then labeled and used to probe cDNAs or oligonucleotides encoding the gene on any of a variety of surfaces; in situ hybridization; and detection of a reporter gene.

Methods to measure protein expression levels generally include, but are not limited to: Western blot, immunoblot, enzyme-linked immunosorbant assay (ELISA), radioimmunoassay (RIA), immunoprecipitation, surface plasmon resonance, chemiluminescence, fluorescent polarization, phosphorescence, immunohistochemical analysis, matrix-assisted laser desorption/ionization time-of-flight (MALDI-TOF) mass spectrometry, microcytometry, microarray, microscopy, fluorescence activated cell sorting (FACS), and flow cytometry, as well as assays based on a property of the protein including but not limited to enzymatic activity or interaction with other protein partners. Binding assays are also well known in the art. For example, a BIAcore machine can be used to determine the binding constant of a complex between two proteins. The dissociation constant for the complex can be determined by monitoring changes in the refractive index with respect to time as buffer is passed over the chip (O'Shannessy et al., 1993, *Anal. Biochem.* 212:457; Schuster et al., 1993, *Nature* 365:343). Other suitable assays for measuring the binding of one protein to another include, for example, immunoassays such as enzyme linked immunoabsorbent assays (ELISA) and radioimmunoassays (RIA); or determination of binding by monitoring the change in the spectroscopic or optical properties of the proteins through fluorescence, UV absorption, circular dichroism, or nuclear magnetic resonance (NMR).

When quantifying gene expression levels of any one or more genes selected from MX1, IFIT1, ISG15 and combinations thereof in a sample from the subject, RNA is extracted from the sample by known standard methods and then the relative gene expression level of each of MX1, IFIT1, and ISG15 is quantified by a method such as quantitative PCR. When using quantitative PCR, primer pairs such as a primer pair having ID No. Hs00182073_m1 (Applied Biosystems) for MX1 or a primer pair having ID No. Hs00192713_m1 (Applied Biosystems) for ISG15 and/or a primer pair consisting of a forward primer consisting of SEQ ID NO:1 and a first reverse primer consisting of SEQ ID NO:2 for IFIT1 can be used. Human GADPH can be used an endogenous control for the quantitative PCR method. The relative ISG expression level is then multiplied by $10^5$ to convert all of the relative expression values to greater than 1 (herein referred to as log transformation). Next, the log transformed relative expression levels are averaged to obtain the overall gene expression level. Further, the overall gene expression level can be compared to a control or reference expression level. High or low expression groups are defined as one standard deviation above or below the mean, respectively. The control or reference group levels are within one standard deviation of the mean.

When comparing the expression level of any one or more genes selected from MX1, IFIT1, ISG15 and combinations thereof in a sample from the subject to a reference or control level, it is to be understood that the expression level of the any one or more genes is compared with the same gene or genes from the reference or control. For example, if the expression level of MX1 and IFIT1 are both determined or analyzed, then the expression level of MX1 from the subject would be compared to the expression level of MX1 from the reference and likewise, the expression level of IFT1 from the subject would be compared to the expression level of IFT1 from the reference. The expression level of any one or more genes as disclosed herein is considered altered if the expression level of the one or more genes as compared to the expression level of the same one or more genes from the reference is increased or decreased (upregulated or downregulated) as compared to the control or reference level.

In one aspect, the expression levels of one, two or three, or at least two, or at least three of the ISG genes disclosed herein are altered (i.e. increased, decreased or be a combination of expression levels) as compared to the corresponding genes from a reference level, wherein one or more of the gene expression levels is increased (or the genes are upregulated) as compared to the reference expression level, while one or more different gene expression levels is decreased (or the genes are downregulated) as compared to the reference expression level.

In yet another aspect, it is contemplated that the expression level of one or more genes of other members of the ISG gene family (see Table 2 in Example section) is determined in addition to the expression level MX1, IFIT1 and/or ISG15. The expression level of the one or more genes of the other ISG family members is compared to the expression level of the same ISG expression level from a reference or control.

In one aspect, an increased expression level is determined when the subject's ISG gene expression level of the one or more of the ISG genes disclosed herein is at least greater than one standard deviation (also defined as one standard deviation from or beyond the mean) from the mean as compared to the control or reference and/or is determined to be significantly different (such as statically significantly different).

In yet another aspect, a decreased expression level is determined when the subject's ISG gene expression level of the one or more of the ISG genes disclosed herein is at least less than one standard deviation from the mean (also defined as one standard deviation from or beyond the mean) as compared to the control and/or reference and/or is determined to be significantly different (such as statically significantly different).

In still other aspects, the relative gene expression level of the one or more ISG genes is at least about 5%, at least about 10%, at least about 20%, at least about 30%, at least about 40%, at least about 50%, at least about 60%, at least about 70%, at least about 80%, at least about 90%, or 100% different (i.e. increased or decreased) from the expression level of the reference/control. In still another aspect, the gene expression level of the one or more genes is at least about a 2 fold, at least about a 3 fold, at least about a 4 fold, at least about a 5 fold, at least about a 10-fold, at least about a 20 fold, at least about a 25 fold, at least about a 30 fold, at least about a 40 fold or at least about a 50 fold difference from the expression level of the reference/control.

In yet another aspect, the overall gene expression level of two or more ISG genes is at least about 5%, at least about 10%, at least about 20%, at least about 30%, at least about 40%, at least about 50%, at least about 60%, at least about 70%, at least about 80%, at least about 90%, or 100% different (i.e. increased or decreased) from the expression level of the reference/control. In still another aspect, the overall gene expression level of two or more ISG genes is at least about a 2 fold, at least about a 3 fold, at least about a 4 fold, at least about a 5 fold, at least about a 10-fold, at least about a 20 fold, at least about a 25 fold, at least about a 30 fold, at least about a 40 fold or at least about a 50 fold difference from the expression level of the reference/control.

As used herein, reference to a reference or control, means a subject who is a relevant reference or control to the subject being evaluated by the methods of the present invention. The control can be matched in one or more characteristics to the subject. More particularly, the control can be matched in one or more of the following characteristics, gender, age, race, body mass index (BMI) and/or disease state. The reference or control expression level used in the comparison of the methods of the present invention can be determined from one or more relevant reference or control subjects. The control expression level is the mean expression level of the same ISGs predetermined from a reference level known to correlate with severe ARDS.

Another embodiment of the present invention relates to a kit for detecting the expression of one or more ISG genes. In one aspect, the kit comprises a detection agent for detecting the expression one or more of the genes. In one aspect, the kit comprises an agent for detecting mRNA expression of one or more of the genes. In still another aspect, the kit comprises an agent for detecting protein expression of one or more of the genes.

As disclosed in the examples presented herein the single-center study by the inventors is the first known exploration of the clinical significance of systemic ISG expression in ARDS. In a training set of patients (n=31) the inventors identified three ISGs that account for the greatest variability in expression. These genes MX1, ISG15, and IFIT1 are prototypical ISGs, previously shown to be highly expressed in stimulated neutrophils (Malcolm K C, et al. (2003) Microarray analysis of lipopolysaccharide-treated human neutrophils. Am J Physiol Lung Cell Mol Physiol 284: L663-670.; Fessler M B, et al. (2002) A Genomic and Proteomic Analysis of Activation of the Human Neutrophil by Lipopolysaccharide and Its Mediation by p38 Mitogen-activated Protein Kinase. J Biol Chem 277: 31291-31302.; Wright H J, et al. (2008) Periodontitis associates with a type 1 IFN signature in peripheral blood neutrophils. J Immunol 181: 5775-5784.), lymphocytes (Halminen M, et al. (1997)

Expression of MxA protein in blood lymphocytes discriminates between viral and bacterial infections in febrile children. Pediatr Res 41: 647-650.), peripheral blood mononuclear cells (Ramilo O, et al. (2007) Gene expression patterns in blood leukocytes discriminate patients with acute infections. Blood 109: 2066-2077.; Zaas A K, et al. (2009) Gene expression signatures diagnose influenza and other symptomatic respiratory viral infections in humans. Cell Host Microbe 6: 207-217.), and whole blood (Landolt-Marticorena C, et al. (2009) Lack of association between the interferon-alpha signature and longitudinal changes in disease activity in systemic lupus erythematosus. Ann Rheum Dis 68: 1440-1446.). Using this 3-gene panel in a non-overlapping test set (n=120), the inventors found that ARDS patients with ISG expression greater or less than one standard deviation from the mean had significantly worse clinical outcomes, such as an increase rate of death, lower rate of discharge to home, increase in viral and/or bacterial infections, increase need for assisted breathing (i.e. ventilator) and or an increase stay in the ICU. At the time of admission, these three cohorts (low-ISG, mid-range ISG, high ISG) were indistinguishable with regards to age, gender, co-existing medical conditions, or type of physiologic injury.

Figure 4:
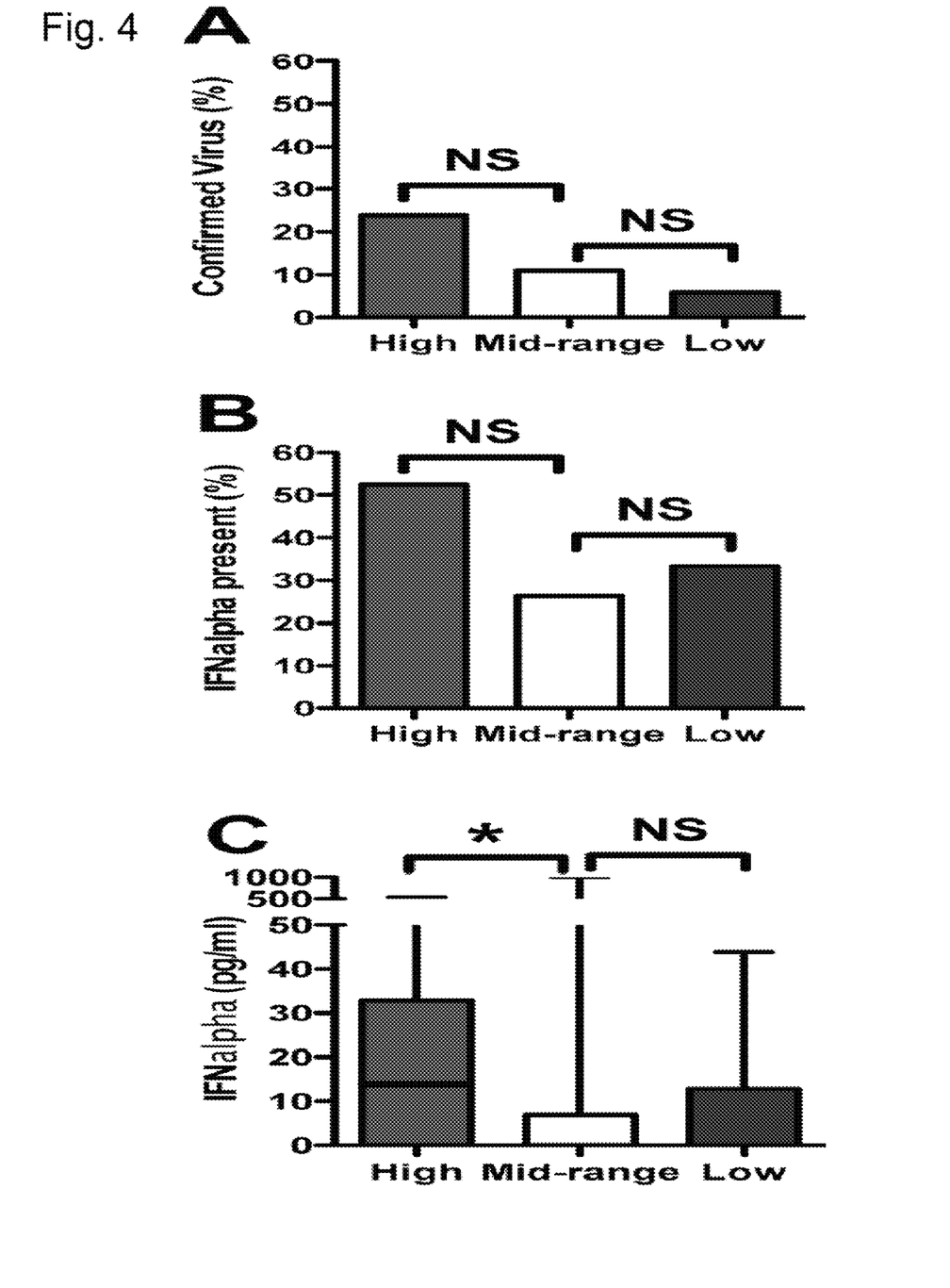
FIG. 4A shows the presence of a viral infection (percent of subjects), as determined either through available medical history or within the course of clinical care, did not reach significance in the cohort with high ISG expression compared to the mid-range and low cohorts (Fisher's exact test p=0.23).
FIG. 4B shows the detection of circulating IFNα trended to occur more frequently within the high ISG cohort compared to the mid-range and low cohorts, but this difference did not reach significance (Fisher's exact test p=0.08).
FIG. 4C shows the levels of circulating IFNα trended higher within the high ISG cohort compared to the mid-range, (Kruskal Wallis overall p-value=0.03; high vs. mid-range pairwise p=0.009). Plot depicts range (minimum=0, maximum=upper whisker), $1^{st}$ to $3^{rd}$ quartile (box) and median (line).

Occurrence of high ISG expression in a subgroup of ARDS patients and healthy controls is not surprising. Acute and chronic viral infections are common within the population (Kumthip K, et al. (2012) Hepatitis C virus NS5A disrupts STAT1 phosphorylation and suppresses type I interferon signaling. J Virol 86: 8581-8591.), and may remain undiagnosed or indolent. While a higher prevalence of acute or chronic viral infection were identified in the high ISG group of ARDS patients (FIG. 4), most of the high ISG group were not known to have a co-existing viral infection. Conversely, patients with proven viral infections were also found (in lower percentages) in the mid-range and low ISG expression cohorts, underscoring the relatively poor correlation between clinically evident viral infections and systemic ISG expression. IFN$\alpha$/$\beta$ is released into the circulation early after viral infections, and may be undetectable or present in very low quantities, even in experimental settings (Roers A, et al. (1994) MxA gene expression after live virus vaccination: a sensitive marker for endogenous type I interferon. J Infect Dis 169: 807-813.). Thus direct testing for IFN$\alpha$/$\beta$ in the serum is not clinically useful. However, leukocyte ISG expression has been identified as a more sensitive marker of Type 1 IFN release (Roers A, et al. (1994) MxA gene expression after live virus vaccination: a sensitive marker for endogenous type I interferon. J Infect Dis 169: 807-813.). ISG expression signatures have been proposed as a useful marker to distinguish between bacterial and viral infections (Ramilo O, et al. (2007) Gene expression patterns in blood leukocytes discriminate patients with acute infections. Blood 109: 2066-2077.), and even between specific viruses (Zaas A K, et al. (2009) Gene expression signatures diagnose influenza and other symptomatic respiratory viral infections in humans. Cell Host Microbe 6: 207-217.) as part of a paradigm shift to focus on host gene profiles to diagnosis infections rather than the traditional search for the pathogen (Ramilo O, Mejias A (2009) Shifting the paradigm: host gene signatures for diagnosis of infectious diseases. Cell Host Microbe 6: 199-200.).

The association of worse clinical outcomes with high ISG expression in ARDS is supported by clinical observations and animal models that demonstrate viral infections increase susceptibility to secondary bacterial infections (McNamee L A, Harmsen A G (2006) Both influenza-induced neutrophil dysfunction and neutrophil-independent mechanisms contribute to increased susceptibility to a secondary *Streptococcus pneumoniae* infection. Infect Immun 74: 6707-6721.; Brundage J F (2006) Interactions between influenza and bacterial respiratory pathogens: implications for pandemic preparedness. Lancet Infect Dis 6: 303-312.; Brundage J F, Shanks G D (2008) Deaths from bacterial pneumonia during 1918-19 influenza pandemic. Emerg Infect Dis 14: 1193-1199.; Metzger D W, Sun K (2013) Immune dysfunction and bacterial coinfections following influenza. J Immunol 191: 2047-2052.; Sun K, Metzger D W (2008) Inhibition of pulmonary antibacterial defense by interferon-gamma during recovery from influenza infection. Nat Med 14: 558-564.; Rothberg M B, et al. (2008) Complications of viral influenza. Am J Med 121: 258-264.; Sellers T F, Jr., Schulman J, Bouvier C, Mc C R, Kilbourne E D (1961) The influence of influenza virus infection on exogenous staphylococcal and endogenous murine bacterial infection of the bronchopulmonary tissues of mice. J Exp Med 114: 237-256.; McCullers J A (2006) Insights into the interaction between influenza virus and pneumococcus. Clin Microbiol Rev 19: 571-582.). Primary or secondary bacterial infections precipitate an overwhelming majority of ARDS cases (Matthay M A, et al. (2012) The acute respiratory distress syndrome. J Clin Invest 122: 2731-2740.). Previously, the inventors found that ARDS neutrophils with elevated ISG expression have an altered response to *S. aureus*, which included reduced p38 MAP kinase activation, attenuation of $O_2^-$ generation and IL8 secretion, increased apoptosis, and impaired bacterial killing (Malcolm K C, et al. (2011) Bacteria-Specific Neutrophil Dysfunction Associated with Interferon-Stimulated Gene Expression in the Acute Respiratory Distress Syndrome. PLoS 6: e21958.). Others have reported IFN$\alpha$/$\beta$ release and ISGs expression promote antibacterial activity against select pathogens (Mancuso G, et al. (2007) Type I IFN signaling is crucial for host resistance against different species of pathogenic bacteria. J Immunol 178: 3126-3133.; Carrero J A, et al. (2004) Type I interferon sensitizes lymphocytes to apoptosis and reduces resistance to *Listeria* infection. J Exp Med 200: 535-540.; O'Connell R M, et al. (2004) Type I interferon production enhances susceptibility to *Listeria* monocytogenes infection. J Exp Med 200: 437-445.; Kelly-Scumpia K M, et al. (2010) Type I interferon signaling in hematopoietic cells is required for survival in mouse polymicrobial sepsis by regulating CXCL10. J Exp Med 207: 319-326.). No demographic or clinical feature at study enrollment predicted worse outcomes in the high ISG expression compared with the mid-range group, with the exception of a greater prevalence of African Americans in the high ISG group (19% vs 2.4%, p=0.015). African Americans have been found to experience worse outcomes from ARDS (Moss M, Mannino D M (2002) Race and gender differences in acute respiratory distress syndrome deaths in the United States: an analysis of multiple-cause mortality data (1979-1996). Crit Care Med 30: 1679-1685.). However, multivariate analysis of the test set presented herein confirmed that ISG expression was still a risk factor after accounting for race in the high expression cohort.

The presence of a distinct subpopulation of ARDS patients with relatively inhibited ISG expression was seen both within the training set and the test set. Outcomes in this cohort were also worse than the mid-range ISG group, without differences in demographic or clinical features. The low ISG group had a normal BMI, which was significantly lower than the mid-range group, who were on average overweight (mean±sd: 24.0±4.5 vs 28.7±6.5, p=0.006). However, the prevalence of pre-existing medical conditions was not greater in the low-ISG subgroup, and differences in BMI within this range are not associated with changes in outcomes from ARDS (Morris A E, et al. (2007) The association between body mass index and clinical outcomes in acute lung injury. Chest 131: 342-348.). Worse outcomes in ARDS patients with abnormally low ISG expression is supported by a preponderance of data that indicate ISG expression is generally a protective mechanism (Schoggins J W, et al. (2011) A diverse range of gene products are effectors of the type I interferon antiviral response. Nature 472: 481-485.). In the absence of ISG-encoded products, the host is more vulnerable to sustained or recurrent viral infection (Sadler A J, Williams B R (2008) Interferon-inducible antiviral effectors. Nat Rev Immunol 8: 559-568.). Increasingly, viruses have been identified with the capacity to suppress ISG expression through a variety of mechanisms, including strains of herpes simplex virus I (Eidson K M, et al. (2002) Expression of herpes simplex virus ICP0 inhibits the induction of interferon-stimulated genes by viral infection. J Virol 76: 2180-2191.), rhinovirus (Kotla S, et al. (2008) Attenuation of the type I interferon response in cells infected with human rhinovirus. Virology 374: 399-410.), hepatitis C (Kumthip K, et al. (2012) Hepatitis C virus NS5A disrupts STAT1 phosphorylation and suppresses type I interferon signaling. J Virol 86: 8581-8591.; Bode J G, et al. (2007) Subversion of innate host antiviral strategies by the hepatitis C virus. Arch Biochem Biophys 462: 254-265.) and pseudorabies virus (Brukman A, Enquist L W (2006) Suppression of the interferon-mediated innate immune response by pseudorabies virus. J Virol 80: 6345-6356.). A recent trial demonstrated a reduction in ARDS mortality associated with the administration of IFN-beta-1a (Bellingan G, et al. (2014) The effect of intravenous interferon-beta-1a (FP-1201) on lung CD73 expression and on acute respiratory distress syndrome mortality: an open-label study. Lancet Respir Med 2: 98-107.), supporting the inventors results that a subpopulation of ARDS patients with high mortality have low ISG expression.

The inventors have found that systemic ISG expression within the first days of ARDS onset is a predictor of disease severity and prognosis. This response can be considered along with other identified genetic, environmental, and complex demographic factors as a contributor to heterogeneity of ARDS outcomes. Other identified disease modifiers, such as age, race, or alcoholism (Iribarren C, et al. (2000) Cigarette smoking, alcohol consumption, and risk of ARDS: a 15-year cohort study in a managed care setting. Chest 117: 163-168.; Calfee C S, et al. (2011) Active and passive cigarette smoking and acute lung injury after severe blunt trauma. Am J Respir Crit Care Med 183: 1660-1665.; Hudson L, et al. (1995) Clinical risk for development of the acute respiratory distress syndrome. Am J Respir Crit Care Med 151: 293-301.; Moss M, et al. (1996) The role of chronic alcohol abuse in the development of acute respiratory distress syndrome in adults. Jama 275: 50-54.; Milberg J A, Davis D R, et al. (1995) Improved survival of patients with acute respiratory distress syndrome (ARDS): 1983-1993. Jama 273: 306-309.; Ely E W, et al. (2002) Recovery rate and prognosis in older persons who develop acute lung injury and the acute respiratory distress syndrome. Ann Intern Med 136: 25-36.; Kangelaris K N, et al. (2012) The association between a Darc gene polymorphism and clinical outcomes in African American patients with acute lung injury. Chest 141: 1160-1169.; Moss M, Mannino D M (2002) Race and gender differences in acute respiratory distress syndrome deaths in the United States: an analysis of multiple-cause mortality data (1979-1996). Crit Care Med 30: 1679-1685.; Rubenfeld G D, et al. (2005) Incidence and outcomes of acute lung injury. N Engl J Med 353: 1685-1693.), or coding variation in inflammatory response regulating genes (Matthay M A, et al. (2012) The acute respiratory distress syndrome. J Clin Invest 122: 2731-2740.; Gao L, Barnes K C (2009) Recent advances in genetic predisposition to clinical acute lung injury. Am J Physiol Lung Cell Mol Physiol 296: L713-725.; Arcaroli J, et al. (2005) Genetic Polymorphisms And Sepsis. Shock 24: 300-312.), are generally chronic or permanent risk factors. Yet no risk factor is apparent in many ARDS patients, and the general lack of recurrent ARDS argues for the existence of transient risk factor(s). Up or downregulation in ISG expression, following a viral infection or from other causes, could represents a "window" of vulnerability that places an otherwise healthy subject at increased risk for a period of days or weeks. This is a clinically plausible scenario in many patients, supported by analysis of mortality from respiratory failure during viral pandemics (Brundage J F (2006) Interactions between influenza and bacterial respiratory pathogens: implications for pandemic preparedness. Lancet Infect Dis 6: 303-312.; Brundage J F, Shanks G D (2008) Deaths from bacterial pneumonia during 1918-19 influenza pandemic. Emerg Infect Dis 14: 1193-1199.). While ISG expression was assessed early after clinical presentation in the examples presented herein, cytomegalovirus reactivation may occur 1-2 weeks after hospitalization in critically ill patients (Limaye A P, et al. (2008) Cytomegalovirus reactivation in critically ill immunocompetent patients. JAMA 300: 413-422.), which could upregulate ISG expression later in ARDS. Longitudinal studies may determine the duration of abnormal ISG expression in ARDS patients, and if late upregulation occurs with CMV reactivation. While ISG expression may be of prognostic value at the onset of ARDS, this marker may be used to modify clinical care, either by alerting clinicians to the possibility of an unsuspected viral or autoimmune disease, or as a direct target for immunomodulation through administration of Type I interferons (Bellingan G, et al. (2014) The effect of intravenous interferon-beta-1a (FP-1201) on lung CD73 expression and on acute respiratory distress syndrome mortality: an open-label study. Lancet Respir Med 2: 98-107.) and provide different treatment options for patients falling within the various subgroups.

The following examples are provided for illustrative purposes, and are not intended to limit the scope of the invention as claimed herein. Any variations which occur to the skilled artisan are intended to fall within the scope of the present invention. All references cited in the present application are incorporated by reference herein to the extent that there is no inconsistency with the present disclosure.

EXAMPLES

Material and Methods
Study Enrollment
Training Set of ISG expression: Gene expression data from peripheral blood neutrophils isolated from patients with sepsis-induced ARDS (n=31) was used to form the training set. Neutrophils were isolated within 24 hours of meeting criteria for ARDS criteria. Gene expression analysis from a subset of this cohort were previously reported in an analysis of HMGB1 and LPS induced patterns of gene expression in ARDS (Brazma A, et al. (2001) Minimum information about a microarray experiment (MIAME)-toward standards for microarray data.

Nat Genet 29: 365-371.). Gene expression data was also analyzed from healthy volunteers (n=19).

Test Set of ISG expression: Prospective evaluation of ISG expression from circulating neutrophils of ARDS patients (n=120) was performed on patients enrolled into one of four NHLBI ARDS Network studies. The parent studies were: Drug Study of Albuterol to Treat ALI (ALTA, ClinicalTrials.gov Identifier: NCT00434993) (Matthay M A, et al. (2011) Randomized, placebo-controlled clinical trial of an aerosolized beta(2)-agonist for treatment of acute lung injury. Am J Respir Crit Care Med 184: 561-568.), Early Versus Delayed Enteral Feeding and Omega-3 Fatty Acid/Antioxidant Supplementation for Treating People With ALI or ARDS (EDEN-Omega Study: NCT00609180), or Early Versus Delayed Enteral Feeding to Treat People With ALI or ARDS (The EDEN Study: NCT00883948) (Rice T W, et al. (2012) Initial trophic vs full enteral feeding in patients with acute lung injury: the EDEN randomized trial. Jama 307: 795-803.; Rice T W, et al. (2011) Enteral omega-3 fatty acid, gamma-linolenic acid, and antioxidant supplementation in acute lung injury. Jama 306: 1574-1581.), or Statins for Acutely Injured Lungs From Sepsis (SAILS: NCT00979121). The proportion of patients enrolled from each parent study was not different between the cohorts with high, mid-range, or low ISG expression (definitions for these groups described below) (Table 1). None of the interventions tested in the parent studies resulted in a treatment benefit (Matthay M A, Brower R G, Carson S, Douglas I S, Eisner M, et al. (2011) Randomized, placebo-controlled clinical trial of an aerosolized beta(2)-agonist for treatment of acute lung injury. Am J Respir Crit Care Med 184: 561-568.; Rice T W, et al. (2012) Initial trophic vs full enteral feeding in patients with acute lung injury: the EDEN randomized trial. Jama 307: 795-803.; Rice T W, et al. (2011) Enteral omega-3 fatty acid, gamma-linolenic acid, and antioxidant supplementation in acute lung injury. Jama 306: 1574-1581.). The central inclusion criteria for all of these studies was that within a 24-hour time period patients demonstrate an acute onset of hypoxia ($PaO_2/FiO_2 \leq 271$—adjusted for Denver altitude of 1600 m), bilateral infiltrates by chest radiograph, and requirement for intubation and positive pressure ventilation in the absence of evidence for left-sided cardiac failure. All patients enrolled into the parent ARDS Network studies were eligible for this ancillary study. Peripheral blood samples were obtained 2.4±1.1 (mean±S.D.) days after ARDS criteria were met (2.6±1.2 days after intubation). Sample processing and data analysis was performed. Diagnostic testing for acute or chronic viral infections was performed in the context of clinical care, and not as part of the study protocol. There were no common subjects between the training and test sets.

TABLE 1

ARDS Net Study Enrollment Numbers (%) By ISG Group

| Study | Mid-range ISG (n = 82) | High ISG (n = 21) | Low ISG (n = 17) | p-value[a] |
|---|---|---|---|---|
| ALTA | 14 (17.1) | 5 (23.8) | 3 (17.7) | p = 0.72 |
| EDEN/OMEGA | 58 (70.7) | 15 (71.4) | 14 (82.4) | p = 0.64 |
| SAILS | 14 (17.1) | 1 (4.8) | 0 (0) | p = 0.09 |

[a]P-value corresponds to Fisher's exact test for categorical variables comparing three groups.

ISG expression in healthy controls: Volunteers (n=40) were administered an 18-point questionnaire to verify they were not experiencing any acute symptoms of a viral illness, did not have any recently diagnosed medical problems, vaccinations, underlying chronic conditions, or had recently received blood products. In addition, these healthy subjects were verified to have negative screening results for hepatitis B and HIV within 6 months of the blood collection. Vital signs checked on the day of the collection were within the normal range.

Isolation of neutrophils and RNA: Neutrophils were isolated from peripheral blood using the plasma Percoll method (Haslett C, Guthrie L A, Kopaniak M, Johnston R B, Jr., Henson P M (1985) Modulation of multiple neutrophil functions by trace amounts of bacterial LPS and by preparative methods. Am J Pathol 119: 101-110.) in an identical fashion for healthy subjects and ARDS patients. Cells were confirmed to be >95% pure by visual inspection of cytospins. RNA was extracted immediately from $10\text{-}20 \times 10^6$ isolated neutrophils using an RNA extraction reagent TRIZOL ® reagent (Malcolm K C, Arndt P G, Manos E J, Jones D A, Worthen G S (2003) Microarray analysis of lipopolysaccharide-treated human neutrophils. Am J Physiol Lung Cell Mol Physiol 284: L663-670.).

Whole transcriptome analysis of neutrophil ISG expression (training set): Samples were obtained from 31 patients and 19 healthy volunteers. Briefly, total RNA was stabilized in freshly isolated neutrophils by resuspension of $2 \times 10^7$ cells in 1 mL of a stabilization solution RNALATER® (Ambion, Austin, Tex.), then stored at −20° C. Subsequent isolation with an RNA extraction reagent TRIZOL® (Life Technologies, Rockville, Md.) and purification with spin columns RNEASY® MINELUTE® columns) (Qiagen, Valencia, Calif.) was performed following the manufacturer's protocol. Between 1 and 5 μg of total RNA was used for microarray target labeling using standard methods for reverse transcription and one round of in vitro transcription (Golpon H A, Coldren C D, Zamora M R, Cosgrove G P, Moore M D, et al. (2004) Emphysema lung tissue gene expression profiling. Am J Respir Cell Mol Biol 31: 595-600.). HG-U133A microarrays were hybridized with 10 μg cRNA and processed per the manufacturer's protocol (Affymetrix, Foster City, Calif.). Experiments for this study were performed as recommended by the Microarray Gene Expression Data society (Brazma A, Hingamp P, Quackenbush J, Sherlock G, Spellman P, et al. (2001) Minimum information about a microarray experiment (MIAME)-toward standards for microarray data. Nat Genet 29: 365-371.). Individual arrays were determined to be of high quality ((2004) Expression profiling-best practices for data generation and interpretation in clinical trials. Nat Rev Genet 5: 229-237.) by: (a) visual inspection; (b) comparison of the overall fluorescence intensity (scaling factor) to other arrays in the group; and (c) low 3'/5' ratios for GAPDH and β-actin (ratio <3). This procedure insures that each of the arrays in the group can be directly compared, and that the input mRNA was intact. Single channel hybridization was performed per sample. The internal quality control for each hybridization included comparison of overall intensity across all arrays (intensity consistently varied within two standard deviations of the median intensity) and the integrity of the labeled target as determined by the ratio of hybridization intensity to 3' and 5' regions of GAPD and β-actin (3'/5' ratios were less than 3 for all arrays). RNA quality was assessed by spectrophotometry (A260/A280>1.8) and Agilent Bioanalyzer (28S/18S rRNA intensity >1.5). Affymetrix Eukaryotic Hybridization Control mixture was employed as external control.

The complete set of gene expression data has been deposited in the GEO database (ncbi.nlm.nih.gov/geo/, accession #GSE3037).

Gene expression analysis of the test set was performed using modules within MeV 4.6 (Saeed A I, et al. TM4: a free, open-source system for microarray data management and analysis. Biotechniques. 2003 February; 34(2):374-8.) Genes included in the "Type I Interferon-mediated Signaling Pathway Cluster" by the Gene Ontology Consortium (GO: 0060337) were analyzed by Significance Analysis for Microarrays to eliminate genes whose expression did not vary between subjects and to detect those genes with significant variation between subjects. Hierarchical clustering was performed on this subset using Euclidean distance and complete linkage. Standard deviation of gene expression was derived from t-test between control and patient samples. Principal Component Analysis was performed on the genes using median centering. These analyses identified Mx1, ISG15, and IFIT1 as genes whose expression differences were the greatest between subjects.

PCR analysis of ISG expression (test set): Test set gene expression was quantified by real-time PCR of MX1, IFIT1, and ISG15 relative to GAPDH by the ΔCt method using standard conditions. Primers and probes were obtained from Applied BioSystems (MX1, Hs00182073_m1; ISG15; Hs00192713_m1; GAPDH Endogenous Control) and Roche (IFIT1, Universal Probe Library #9 and forward: (SEQ ID NO:1 5'-AGAACG-GCTGCCTAATTTACA-3'reverse: SEQ ID NO:2 5'-GCTCCAGACTATCCTTGACCT-3') as described (Malcolm K C, et al. (2011) Bacteria-Specific Neutrophil Dysfunction Associated with Interferon-Stimulated Gene Expression in the Acute Respiratory Distress Syndrome. PLoS 6: e21958). Relative ISG expression was multiplied by $10^5$ to convert all values greater than 1, and ranked by the sum of $\log_2$ transformed expression values for each gene.

Data analysis. Overall group comparisons were made using ANOVA or Kruskal-Wallis tests for continuous variables and Fisher's exact tests for categorical variables, as indicated. Pairwise comparisons were made between the High and Mid-range and Low and Mid-range ISG groups when the corresponding overall test was significant. Ventilator-free and ICU-free days (Schoenfeld D A, Bernard G R, Network A (2002) Statistical evaluation of ventilator-free days as an efficacy measure in clinical trials of treatments for acute respiratory distress syndrome. Crit Care Med 30: 1772-1777.) were analyzed using linear regression. Twenty-eight day home with UAB and mortality and 90-day home with unassisted breathing (UAB) and mortality were modeled using logistic regression. Cox proportional hazards models were used to model time to discharge to home and mortality outcomes. All regression and survival analyses were adjusted for gender, race, age and BMI. P-values corresponding to two-tailed tests that were less than 0.05 were considered statistically significant. Analyses were performed using SAS (Version 9.4, SAS Institute), and plotted using GraphPad Prism software.

Transcriptional Profiling of ISG Expression in ARDS Neutrophils

Genome-wide transcriptional profiles of circulating neutrophils isolated from patients with sepsis-induced ARDS (n=31) and healthy controls (n=19) comprised a training set of ISG expression. Genes identified as the "Type I Interferon-mediated Signaling Pathway Cluster" by the Gene Ontology Consortium (GO:0060337) yielded 66 unique genes with available expression data. Using hierarchical clustering of expression, 3 distinct subject groups and 3 distinct gene groups were identified. Both healthy controls and patients were found distributed in clusters of high and mid-range ISG expression, while only ARDS patients were found within a cluster of low ISG expression.

Figure 1:
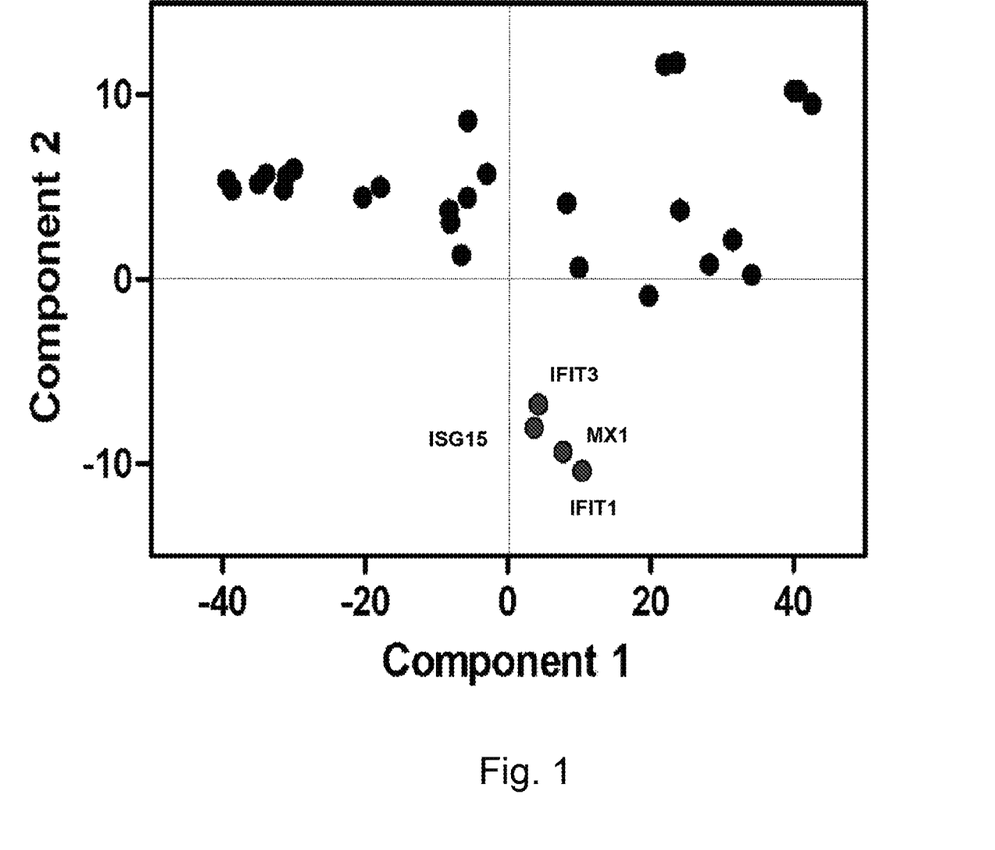
FIG. 1 shows a principal component analysis identifying four genes (MX1, IFIT1, ISG15 and IFIT3) that comprised nearly all of the variability between subjects when the transcriptional signature of ISG expression in a training set of ARDS patients and healthy control neutrophils was determined.

$\log_2$-transformed expression of 31 unique transcripts within the Type I Interferon-mediated Signaling Pathway Cluster from neutrophils isolated from sepsis-induced ARDS patients (n=31) and normal volunteers (n=19). Training set profile is ordered by hierarchical clustering (Euclidean distance with complete linkage) and contained only genes determined to significantly change between subjects (Table 2). Three major gene clusters of subjects were broadly grouped as high ISG expression, mid-range, and low. Only ARDS patients were contained within the low ISG expression subject cluster (data not shown). When the genes were ranked for extent of variance using relative size of the standard deviation between subjects, the 3 genes with the largest variance were identified as MX1, ISG15, and IFIT1. As shown in FIG. 1, a principal component assay identified 4 genes that comprised nearly all of the variability between subjects.

A test for variance was used to identify ISG that were representative of variability between subjects. When these genes were ranked for extent of variance using relative size of the standard deviation between subjects, the 3 genes with the largest variance were identified as MX1, ISG15, and IFIT1 (Group 3 in Table 2). In addition, when gene expression was examined by Principal Component Analysis to discern changes in variation, the three previously identified genes and IFIT3 were identified as a distinct cluster (FIG. 1). PC1 (accounting for 91.6% of the variability) appears to generally represent average expression across subjects (high expression at the low end). PC2 (accounting for 4.5%) appears to distinguish genes by variability, where genes with the highest variability are at the low end; there is a clear separation of 4 genes (IFIT3, ISG15, MX1, IFIT1) from the others.

TABLE 2

| ISG Genes | | | |
|---|---|---|---|
| Group 1 High ISG expression | Group 2 Mid-range ISGexpression | Group 3 Highest variability ISG expression | Group 4 Low ISG expression |
| IFITM2 | PSMB8 | IFIT1 | IFI35 |
| HLA-A | SP100 | MX1 | IRF3 |
| HLA-E | ISGF3G | ISG15 | EGR1 |
| HLA-G | STAT1 | IFIT3 | IFI6 |
| HLA-F | MX2 | | OAS1 |
| IFITM3 | ISG20 | IRF7* | OAS2 |
| IFITM1 | | OASL* | IFI27 |
| ADAR | | OAS3* | LOC727996 |
| GBP2 | | | IRF5 |

*also cluster to the variable genes but show less variation

ISG Expression in Neutrophils Isolated from ARDS Patients and Healthy Controls

Figure 2:
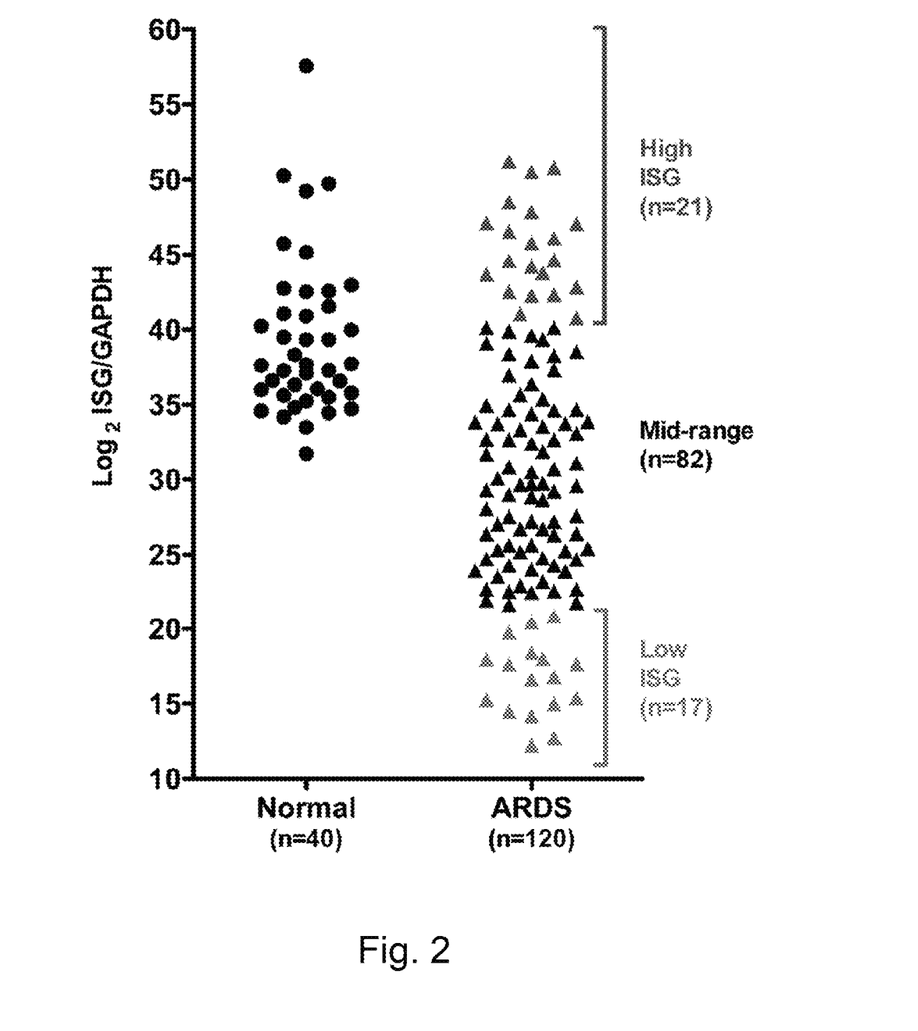
FIG. 2 shows the classification of ARDS patients in a test set based on neutrophil ISG expression. Sum of $\log_2$ transformation expression of neutrophil MX1, IFIT1, and ISG15 from the ARDS patient test set (triangle, n=120) or normal subjects (circle, n=40). Subjects within the test set whose ISG expression was greater or less than one standard deviation from the mean were designated as high or low ISG expressers, respectively. Neutrophils isolated from normal subjects whose ISG expression was analyzed in the identical manner, were compared to the ARDS patients. ISG expression in normal subjects overlapped only with the high and mid-range cohorts of ARDS patients.

The three-gene panel identified by the training set as discussed above was used as a marker of overall neutrophil ISG expression in ARDS. Relative expression level of each gene was determined prospectively by quantitative PCR of neutrophils isolated from ARDS patients (n=120). Analyses was performed using genes as separate predictors in models, but as the expression values tended to be correlated between genes, the sum of $\log_2$ transformed expression values for the 3 genes was sufficient as a predictor and yielded better fits than using the separate genes (FIG. 2). Samples greater than one standard deviation above mean expression were designated as the "high" ISG expression cohort (n=21), and the corresponding group of samples with ISG expression less than one standard deviation below the mean was designated as the "low" ISG expression cohort (n=17). Subjects falling within one standard deviation of the mean were designated as "mid-range" ISG expression (n=82) (FIG. 2). ARDS patients in the test set were compared with healthy control subjects (n=40) analyzed in an identical fashion. As with the training set, ISG expression of healthy controls was found to fall only within the high and mid-ranges (FIG. 2), while the low-expressing cohort was confined to subjects with ARDS.

Using the 3 categories for the sum yielded Akaike Information Criterion (AIC) goodness-of-fit values that were at least as good as using the sum itself, or categories based on other criteria (e.g., creating 4 groups based on quartiles, 2 groups based on a split at the mean or median, etc.).

Patient Characteristics at Study Enrollment

Demographic features and underlying medical conditions for ARDS patients were quite similar across cohorts at the time of enrollment (Table 3). Compared to the mid-range cohort, patients with high and low ISG expression were not different in age or gender. Within the high ISG cohort, 19% were identified as Black or African American, compared to 2.4% of the mid-range cohort (pairwise p=0.015). No differences in race or ethnicity were identified in the low ISG cohort compared to mid-range. BMI was significantly lower in the low ISG cohort compared to the mid-range cohort (pairwise p=0.006). However, the low ISG cohort did not have an increased frequency of identified pre-existing medical conditions. Patients with at least one identified underlying medical condition ranged from 63.4% to 71.4% across the three groups (Fisher's test p=0.80).

Identified risk factors for ARDS at presentation were also not different between the study groups (Table 4). The most common presenting injury was pneumonia, with a prevalence ranging from 71.9% to 76.5% between the three groups (Fisher's test p=0.95), followed by secondary sepsis (range 57.1% to 73.2%, Fisher's test p=0.33). No patient had primary trauma. Study enrollment occurred 2.4±1.1 days (mean±S.D.) after meeting ARDS criteria. Clinical and physiologic assessment made at this early time point demonstrated a divergence in disease severity (Table 5). While gas exchange as measured by the $PaO_2$ to $FiO_2$ ratio was not different between the three groups, the Glasgow Coma score and the APACHE II score differed significantly, with the mid-range group averaging a less severe score.

TABLE 4

Number (%) Of Injury Etiology at Initial Clinical Presentation by ISG Group

| Primary physiological injury | Mid-range ISG (n = 82) | High ISG (n = 21) | Low ISG (n = 17) | p-value[a] |
| --- | --- | --- | --- | --- |
| Pneumonia-primary | 59 (71.9) | 16 (76.2) | 13 (76.5) | p = 0.95 |
| Pneumonia-secondary | 8 (9.8) | 1 (4.8) | 2 (11.8) | p = 0.71 |
| Aspiration-primary | 6 (7.3) | 1 (4.8) | 2 (11.8) | p = 0.75 |
| Aspiration-secondary | 20 (24.4) | 3 (14.3) | 1 (5.9) | p = 0.18 |
| Multiple transfusions-primary | 3 (3.7) | 0 (0) | 0 (0) | p = 1.0 |
| Multiple transfusions-secondary | 5 (6.1) | 1 (4.8) | 0 (0) | p = 83 |
| Sepsis-primary | 10 (12.2) | 3 (14.3) | 2 (11.8) | p = 0.91 |
| Sepsis-secondary | 60 (73.2) | 12 (57.1) | 12 (70.6) | p = 0.33 |

[a]P-value corresponds to Fisher's exact test for categorical variables comparing three groups.

TABLE 3

Baseline Characteristics of ARDS Patients

| Characteristic | Mid-range ISG (n = 82) | High ISG (n = 21) | Low ISG (n = 17) | p-value[1] |
| --- | --- | --- | --- | --- |
| Male sex no. (%) | 45 (54.9) | 9 (42.9) | 9 (52.9) | p = 0.67 |
| Age in years (mean S.D.) | 53.7 ± 16.2 | 53.4 ± 11.7 | 55.1 ± 14.2 | p = 0.93 |
| White race no. (%) | 63 (76.8) | 14 (66.7) | 10 (58.8) | p = 0.23 |
| Black or African American no. (%) | 2 (2.4) | 4 (19.0) | 2 (11.8) | p = 0.01[b] |
| Hispanic no. (%) | 16 (19.5) | 6 (28.6) | 5 (29.4) | p = 0.45 |
| BMI (mean ± S.D.) | 28.7 ± 6.5 | 29.8 ± 8.1 | 24.0 ± 4.5 | p = 0.02[c] |
| Underlying Medical Conditions | | | | |
| Any Medical Condition (%) | 52 (63.4) | 15 (71.4) | 11 (64.7) | p = 0.80 |
| Chronic dialysis-no. (%) | 1 (1.2) | 1 (4.8) | 2 (11.8) | p = 0.06 |
| AIDS-no. (%) | 2 (2.4) | 2 (9.6) | 0 (0) | p = 0.23 |
| Leukemia[2]-no. (%) | 0 (0) | 0 (0) | 0 (0) | p = 1.0 |
| Non-Hodgkin's lymphoma-no. (%) | 0 (0) | 0 (0) | 0 (0) | p = 1.0 |
| Solid tumor w/ metastasis-no. (%) | 2 (2.4) | 1 (4.8) | 0 (0) | p = 0.68 |
| Immune suppression[3]-no. (%) | 5 (6.1) | 4 (19.1) | 0 (0) | p = 0.06 |
| Hepatic failure[4]-no. (%) | 2 (2.4) | 0 (0) | 0 (0) | p = 1.0 |
| Cirrhosis-no. (%) | 8 (9.8) | 3 (14.3) | 2 (11.8) | p = 0.74 |
| Diabetes Mellitus-no. (%) | 16 (19.5) | 5 (23.8) | 7 (41.2) | p = 0.17 |
| History of hypertension-no. (%) | 29 (35.4) | 8 (38.1) | 6 (35.3) | p = 0.96 |
| Prior myocardial infarction-no. (%) | 5 (6.1) | 1 (4.8) | 2 (11.8) | p = 0.64 |
| Peripheral vascular disease-no. (%) | 3 (3.7) | 1 (4.8) | 1 (5.9) | p = 0.81 |
| Prior stroke with sequelae-no. (%) | 1 (1.2) | 0 (0) | 2 (11.8) | p = 0.07 |
| Dementia-no. (%) | 3 (3.7) | 1 (4.8) | 1 (5.9) | p = 0.56 |
| Chronic pulmonary disease-no. (%) | 9 (11.0) | 2 (9.5) | 0 (0) | p = 0.49 |
| Arthritis-no. (%) | 4 (4.9) | 0 (0) | 0 (0) | p = 0.77 |
| Peptic ulcer disease-no. (%) | 3 (3.7) | 2 (9.5) | 0 (0) | p = 0.34 |

[a]P-value corresponds to overall ANOVA for continuous variables comparing three groups, and Fisher's exact test for categorical variables comparing three groups.
[b]Significant difference between Mid-range and High ISG groups.
[c]Significant differences between Mid-range and Low ISG groups.

TABLE 5

Physiologic Assessment at Enrollment[a], Mean ± SD of Variables by ISG Group

| ASSESSMENT | Mid-range ISG (n = 82) | High ISG (n = 21) | Low ISG (n = 17) | p-value[b] |
|---|---|---|---|---|
| Gas exchange | | | | |
| $PaO_2/FiO_2$ | 107 ± 40.8 | 104 ± 45.1 | 128 ± 53.1 | p = 0.16 |
| APACHE II score | 87.5 ± 22.8 | 106.2 ± 20.4 | 100.1 ± 38.8 | p = 0.006[c] |
| Glascow Coma Score | 8.3 ± 2.8 | 5.7 ± 2.6 | 8.0 ± 3.1 | p = 0.002[c] |

[a]Values measured 2.4 ± 1.1 days (mean ± S.D.) after ARDS criteria met.
[b]P-value corresponds to overall ANOVA for continuous variables comparing three groups.
[c]Significant difference between Mid-range and High ISG groups.

Extremes in ISG Expression are Associated with Decreased Survival and Greater Disease Severity.

Outcomes for patients with high or low ISG expression were compared with the mid-range ISG cohort. High ISG expression was associated with worse outcomes, with fewer ventilator-free and ICU-free days over the first 28 days than the mid-range cohort (pairwise p-values=0.006 and 0.009, respectively, Table 6). The fraction of patients discharged to home with unassisted breathing (UAB) was significantly lower at 90 days for high ISG compared to mid-range (pairwise p-value=0.02, Table 6). Mortality was higher by 90 days for high ISG, with 33.3% reported as dead prior to discharge to home with unassisted breathing for high ISG, compared to 12.2% for the mid-range ISG group (pairwise p-value=0.04).

Patients with low ISG expression also demonstrated worse outcomes, similar in severity to the high ISG expression cohort, with fewer ICU-free days over the first 28 days compared to the mid-range cohort (pairwise p-value=0.02, Table 6). The fraction of patients discharged to home with unassisted breathing was lower at 90 days for low ISG compared to mid-range (pairwise p-value=0.03, Table 6). Mortality was significantly increased at 28 days (pairwise p-value=0.03), and by 90 days, with 35.3% reported as dead prior to discharge to home with unassisted breathing for low ISG (p=0.03 compared to mid-range, Table 6).

Multivariate Analysis of Risk Associated with Extremes in ISG Expression

After adjusting for gender, race, age and BMI, both high and low ISG expression cohorts had significantly fewer days ventilation-free compared to the mid-range ISG cohort (p-values=0.002 and 0.002, respectively, Table 7). Similarly, after adjusting for covariates, both high and low ISG expression cohorts had significantly fewer days ICU-free compared to the mid-range ISG cohort (p-values=0.001 for both comparisons, Table 7). Multivariate analysis was not performed for APACHE II score, as it measures elements of disease severity likely associated with extremes in ISG expression.

Figure 3A:
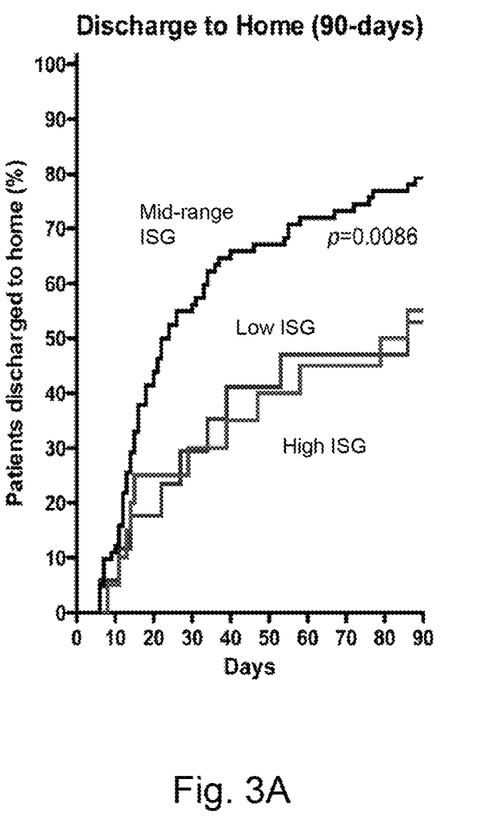
FIG. 3A shows the proportion of patients confirmed to be discharged to home with unassisted breathing within 90 days of study enrollment. Overall Log-Rank p-value comparing groups was 0.009. After adjusting for age, race, gender and BMI, rate of discharge to home was significantly lower for both the high ISG (lighter line, p=0.006) and low ISG (darker line, p=0.004; p-values from Cox PH model) expressing cohorts when compared to the mid-range (darkest line).
Figure 3B:
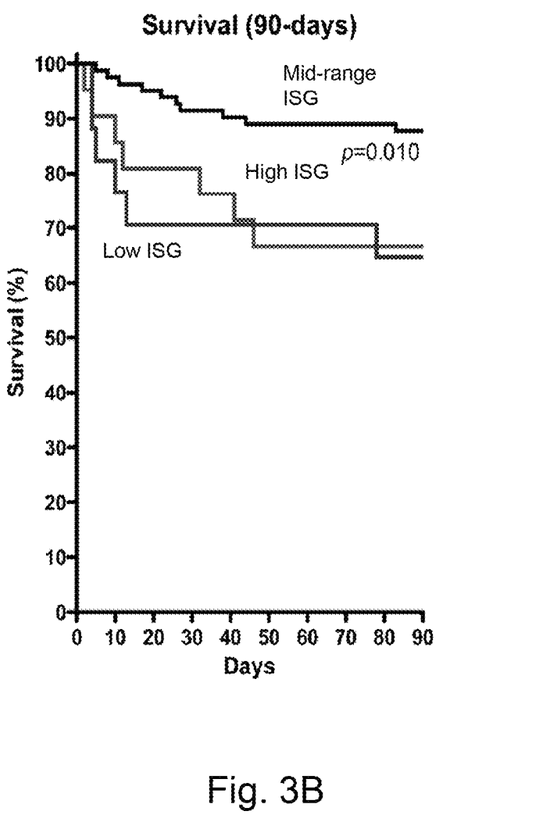
FIG. 3B shows the proportion of patients confirmed to be dead within 90 days of study enrollment. Overall log-rank p-value comparing groups was 0.01. After adjusting for age, race, gender and BMI, rate of death was significantly worse for both the high ISG (lighter line, p=0.02) and low ISG (darker line, p=0.02; p-values from Cox PH model) expressing cohorts when compared to the mid-range (darkest line).

Patients' status of being discharged home with unassisted breathing (UAB) by day 90 was significantly different for high and low ISG expression cohorts, compared to the mid-range cohort (p-values=0.006 and 0.01, respectively, Table 7). Patients' 90 day mortality was significantly different for high and low ISG expression cohorts, compared to the mid-range cohort (p-values=0.01 and 0.035, respectively, Table 7). In addition, time to discharge to home with unassisted breathing was significantly delayed in the high and low cohorts compared to the mid-range cohort (P-values=0.006 and 0.004, respectively, p-values from Cox PH model (FIG. 3A). A survival analysis of time to mortality by day 90 was also significantly different for high and low ISG expression cohorts, compared to the mid-range cohort (p-values=0.01 and 0.0o0, respectively, from Kaplan Meier analysis; adjusted P-values=0.02 and 0.02, respectively, from Cox PH model) (FIG. 3B).

TABLE 6

Summary Statistics for Clinical Outcomes

| Characteristic | Mid-range ISG (n = 82) | High ISG (n = 21) | Low ISG (n = 17) | p-value[a] |
|---|---|---|---|---|
| 28-day free[b] | | | | |
| Ventilation, median (Q1-Q3) | 18 (4-22) | 4 (0-18) | 2 (0-18) | p = 0.006[c] |
| ICU, mean, median (Q) | 17 (6-22) | 1 (0-16) | 1 (0-14) | p = 0.02[c] |
| Home with unassisted breathing | | | | |
| [b]Day 28, No. (%) | 20 (24.4) | 6 (28.6) | 4 (23.5) | p = 0.95 |
| [b]Day 90, No. (%) | 65 (79.3) | 11 (52.4) | 9 (52.9) | p = 0.01[c] |
| Mortality | | | | |
| [b]Day 28, No. (%) | 7 (8.5) | 4 (19.1) | 5 (29.4) | p = 0.04[c] |
| [b]Day 90, No. (%) | 10 (12.2) | 7 (33.3) | 6 (35.3) | p = 0.02[c] |

Elements in table are median (Q1-Q3) or number (percent) as indicated.
[a]P-value corresponds to overall Kruskal-Wallis test for 28-day free data comparing three groups, and Fisher's exact test for categorical variables comparing three groups.
[b]Number of days that patient is both alive and free of mechanical ventilation or ICU care for the first 28 days or first 90 days since start of mechanical ventilation or ICU care.
[c]Significant difference between mid-range and high ISG groups and mid-range and low ISG groups.

TABLE 7

Estimated Differences and Odds Ratios for Adjusted Clinical Outcomes, Between High and Mid-Range or Low and Mid-Range ISG Groups

| Characteristic | High ISG (n = 21) | Low ISG (n = 17) | p-value |
|---|---|---|---|
| 28-day free[a] | | | |
| Ventilation, mean difference, 95% CI | −7.00 (−11.38, −2.62) | −7.52 (−12.33, −2.71) | 0.0006[c] |
| ICU, mean difference, 95% CI | −7.02 (−11.32, −2.72) | −7.71 (−12.43, −2.98) | 0.0004[c] |
| Home with UAB[b] | | | |
| 28 Day Period, odds ratio (% CI) | 1.62 (0.52, 5.05) | 0.94 (0.26, 3.45) | 0.69 |
| 90 Day Period, odds ratio (% CI) | 0.19 (0.06, 0.63) | 0.20 (0.06, 0.73) | 0.004[c] |
| Mortality[b] | | | |
| Day 28, odds ratio (% CI) | 2.83 (0.65, 12.33) | 4.23 (0.94, 18.97) | 0.12 |
| Day 90, odds ratio (% CI) | 4.90 (1.37, 17.52) | 4.29 (1.11, 16.59) | 0.02[c] |

All models adjusted for age, race (African American or other), gender and BMI.
[a]For 28-day free variables, mean differences are High or Low ISG group mean minus Mid-range ISG group mean; p-value corresponds to Type 3 analysis from regression model.
[b]For home with unassisted breathing (UAB) and mortality models, Odds Ratio are odds for High or Low ISG group relative to odds for Mid-range ISG group; p-value corresponds to Type 3 analysis from logistic regression model.
[c]Significant difference between Mid-range and High ISG groups and Mid-range and Low ISG groups.

Association of ISG Expression with Viral Infection or Circulating IFNα

Screening of patients for viral infection was not systemically performed. However, acute or chronic viral infections were detected in 15 test set subjects during clinical care, including H1N1 influenza (n=6), HIV (n=4), Hepatitis B (n=1), Hepatitis C (n=3), or H1N1 combined with Hepatitis C (n=1). While 24% of the high ISG expression cohort had a confirmed viral infection, compared to 11% in the mid-range ISG cohort and 5.9% in the low ISG cohort, these differences were not significant (Fisher's exact test p=0.23) (FIG. 4). Serume IFNα was measured in patients as a possible surrogate to detect viral infection. At enrollment into this protocol, 52.4% of patients in the high ISG cohort had detectable IFNα in their circulation, which trended greater than patients in the mid-range ISG cohort (26.3%) and the low ISG cohort (33.3%, Fisher's exact test p=0.08) (FIG. 4). The quantity of IFNα in circulation was highly variable, but greater in the high ISG cohort (median 13.3 pg/mL, range <0.1 to 544) compared to the mid-range ISG cohort (median <0.1, range <0.1 to 1000, Kruskal Wallis p=0.009), (FIG. 4).

While various embodiments of the present invention have been described in detail, it is apparent that modifications and adaptations of those embodiments will occur to those skilled in the art. It is to be expressly understood, however, that such modifications and adaptations are within the scope of the present invention. All of the documents cited herein are incorporated herein by reference.

What is claimed is:

1. A method of treating a severe form of Acute Respiratory Distress Syndrome (ARDS) in a subject having been diagnosed as having ARDS comprising:
   a. extracting RNA from neutrophils obtained from the subject;
   b. quantifying relative RNA expression levels of each of myxovirus resistance 1 (MXI), interferon-induced protein with tetratricopeptide repeats 1 (IFIT1), and interferon-stimulated 15 kDa protein (ISG15) in the extracted RNA by quantitative PCR;
   c. comparing the RNA expression levels from step b against control RNA expression levels of MX1, IFIT1, and ISG15, wherein the control RNA expression levels are the mean RNA expression levels of the same genes predetermined from a reference level known to correlate with a severe form of ARDS, wherein RNA expression levels from the subject is less than one standard deviation above the mean as compared to the control RNA expression levels identifies the subject has having a severe form of ARDS; and
   d. treating the subject identified in step c comprising administering to the subject a therapeutic effective amount of an ISG enhancing agent selected from the group consisting of interferon-alpha, interferon-beta and type III interferon.

2. The method of claim 1, wherein the subject has been diagnosed or deemed to be at risk for a condition selected from the group consisting of sepsis and bacterial pneumonia.

3. The method of claim 1, wherein the expression levels from the subject are determined within 1 to 4 days after ARDS criteria met.

* * * * *

UNITED STATES PATENT AND TRADEMARK OFFICE
CERTIFICATE OF CORRECTION

PATENT NO. : 10,689,703 B2
APPLICATION NO. : 15/139119
DATED : June 23, 2020
INVENTOR(S) : Jerry A. Nick and Kenneth C. Malcolm

Page 1 of 1

It is certified that error appears in the above-identified patent and that said Letters Patent is hereby corrected as shown below:

In the Claims

In Claim 1, Column 27, Line 8, please delete "myxovirus resistance 1 (MXI), interferon-induced pro-" and insert -- myxovirus resistance 1 (MX1), interferon-induced pro- --

Signed and Sealed this
Twenty-second Day of December, 2020

Andrei Iancu
*Director of the United States Patent and Trademark Office*